United States Patent [19]

Grippi

[11] Patent Number: 5,738,670
[45] Date of Patent: Apr. 14, 1998

[54] BLOOD COLLECTION ASSEMBLY HAVING ADDITIVE DISPENSING MEANS

[75] Inventor: Nicholas A. Grippi, Ramsey, N.J.

[73] Assignee: Becton, Dickinson and Company, Franklin Lakes, N.J.

[21] Appl. No.: 710,586

[22] Filed: Sep. 19, 1996

Related U.S. Application Data

[63] Continuation of Ser. No. 392,003, Feb. 21, 1995, abandoned.
[51] Int. Cl.[6] .................................................. A61B 19/00
[52] U.S. Cl. ........................................ 604/403; 604/415
[58] Field of Search ................................ 604/403–407; 128/763–766, 912

[56] References Cited

U.S. PATENT DOCUMENTS

| 2,449,968 | 9/1948 | Smith . | |
| 2,495,942 | 1/1950 | Nosik | 604/416 |
| 2,615,448 | 10/1952 | Fields | 604/416 |
| 2,808,053 | 10/1957 | Morris | 604/415 |
| 3,901,219 | 8/1975 | Kay | 128/764 |
| 5,108,386 | 4/1992 | Finneran | 604/403 |
| 5,511,558 | 4/1996 | Shepard et al. | 604/403 |

*Primary Examiner*—John G. Weiss
*Assistant Examiner*—Dennis Ruhl
*Attorney, Agent, or Firm*—Richard E. Brown

[57] ABSTRACT

A blood collection assembly includes an evacuated container having an open end with a puncturable stopper therein. A liquid impermeable receptacle in the container contains an additive and is removably immobilized in the stopper. In a method for preparing a blood sample for analysis, the stopper is punctured by a cannula connected to a blood supply. The cannula is then advanced until it contacts and dislodges the receptacle from the stopper causing the additive to be released directly into the container where it mixes with incoming blood.

6 Claims, 7 Drawing Sheets

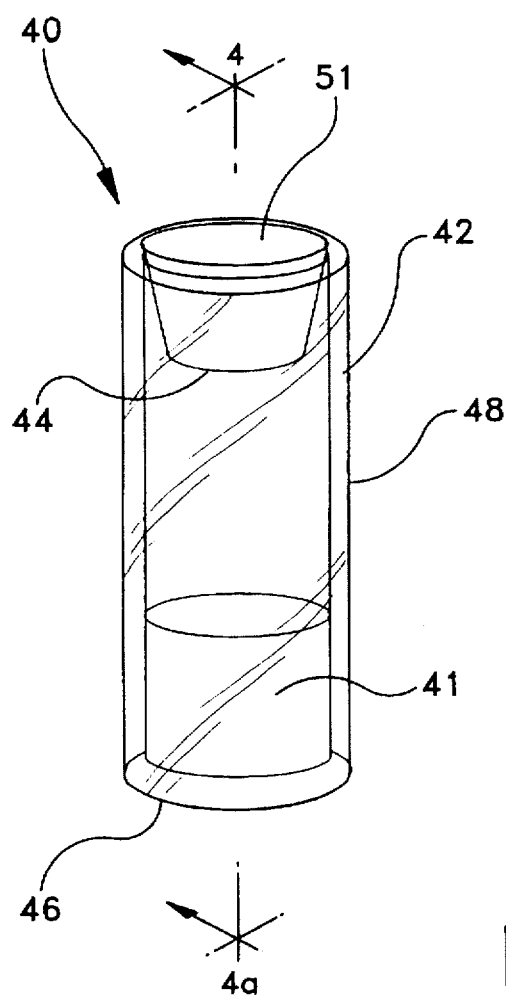
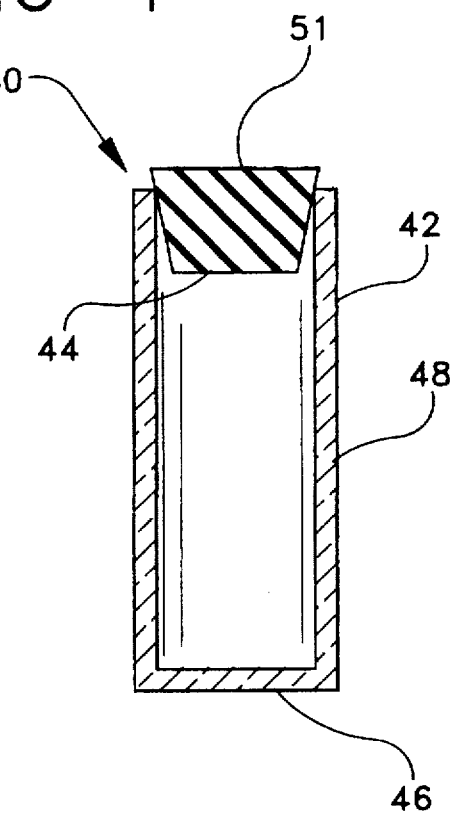
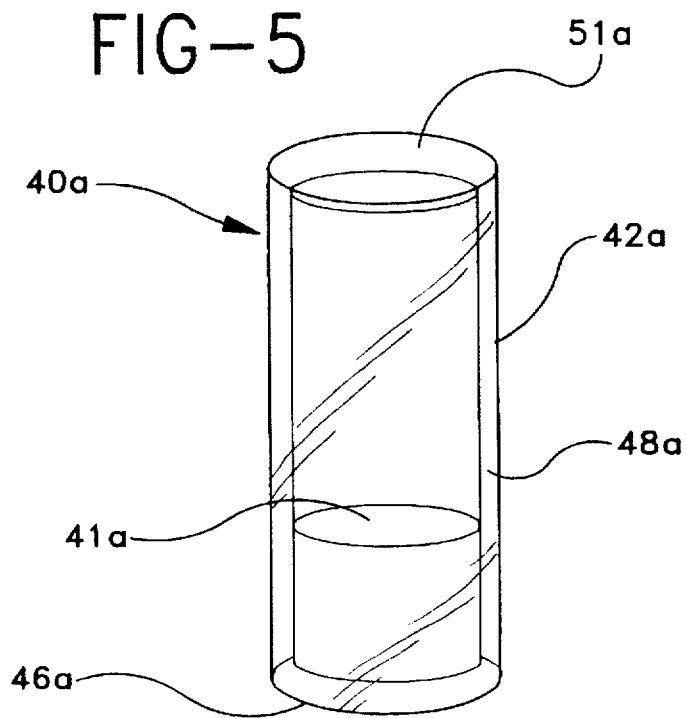

5,738,670

BLOOD COLLECTION ASSEMBLY HAVING ADDITIVE DISPENSING MEANS

This application is a continuation of application Ser. No. 08/392,003, now abandoned filed Feb. 21, 1995.

BACKGROUND OF THE INVENTION

1. Field of the Invention

This invention relates to blood collection, and, more particularly, relates to vacuum actuated tubes and a method for dispensing additives during blood draw.

2. Background

Blood samples are routinely taken in evacuated tubes. One end of a double-ended needle is inserted into a patient's vein. The other end of the needle then punctures a septum covering the open end of the tube so that the vacuum in the tube draws the blood sample through the needle into the tube. Using this technique, a plurality of samples can be taken using a single needle puncture of the skin.

Collection tubes are conventionally made of glass or plastic. Glass tubes have the advantage of liquid and gas impermeability. Plastic tubes are advantageous over glass in lower breakage, less weight in shipment and easier disposal by incineration, but high permeability to liquid and gas is a disadvantage. For example, polyethyleneterephthalate (PET), though widely used commercially for blood collection tubes, has a limited shelf life due to water permeability.

Blood drawn into a tube is typically mixed with an additive present in the tube prior to draw. Clot activators such as silica particles promote rapid coagulation so that the liquid serum fraction can be readily separated from the clotted cells. Anticoagulants, such as sodium citrate, heparin or ethylenediaminetetraacetic acid (EDTA) are used to prevent clotting when the blood sample is to be used directly in hematological tests or to separate blood cells from the plasma.

The additive, whether procoagulant for clot activation or anticoagulant for clotting inhibition, must be rapidly and thoroughly mixed with the blood sample, and if in solution, must be present in a precise concentration to obtain reliable tube-to-tube performance. Various approaches have been disclosed in the art for maintaining additive concentrations. Tubes with thicker walls have been proposed, but these tubes have reduced blood volume capacity. Some manufacturers store liquid additives in a separate barrier package, such as a foil pouch. This approach has several disadvantages, such as additive deterioration after the package is opened. Most recently, the industry has been pursuing development of barrier coatings, usually of silicon dioxide, over the tubes to reduce moisture transmission. This approach increases costs and thus far has met with limited success.

There is a need in the art of blood collection for a means of accurate storage and dispensing of liquid tube additives that maintains additive concentrations and permits use of different plastics for tube manufacture. The present invention fulfills this need.

SUMMARY OF THE INVENTION

An assembly for collecting a blood sample includes an evacuated container, preferably plastic, having an open end with a puncturable stopper therein. A moisture impermeable receptacle in the container has a side wall and an integral bottom end and has a liquid additive for blood analysis therein. The preferred receptacle is removably positioned in the container below the stopper by an interference fit within a skirt of the stopper.

Another aspect of the invention is a method for preparing a blood sample for analysis using the assembly. The stopper is punctured by a cannula connected to a blood supply. The cannula dislodges the receptacle from the stopper so that the additive is discharged into the tube where it mixes with blood entering the tube through the cannula due to the pressure differential between the blood supply and the evacuated container.

Thus the liquid additive may be precisely measured and stored in a water impermeable receptacle which prevents any concentration changes even though a water permeable plastic is used for the container. The additive is thoroughly mixed with the blood during draw and completely discharged into the container in a procedure independent of phlebotomist technique.

BRIEF DESCRIPTION OF THE DRAWINGS

FIG. 3 is a perspective view of the receptacle of FIG. 1;

FIG. 4 is a vertical sectional view of the receptacle of FIG. 3 taken along the line 4–4a thereof;

FIG. 5 is a perspective view of an alternate embodiment of the receptacle of FIG. 1;

DETAILED DESCRIPTION

Figure 1:
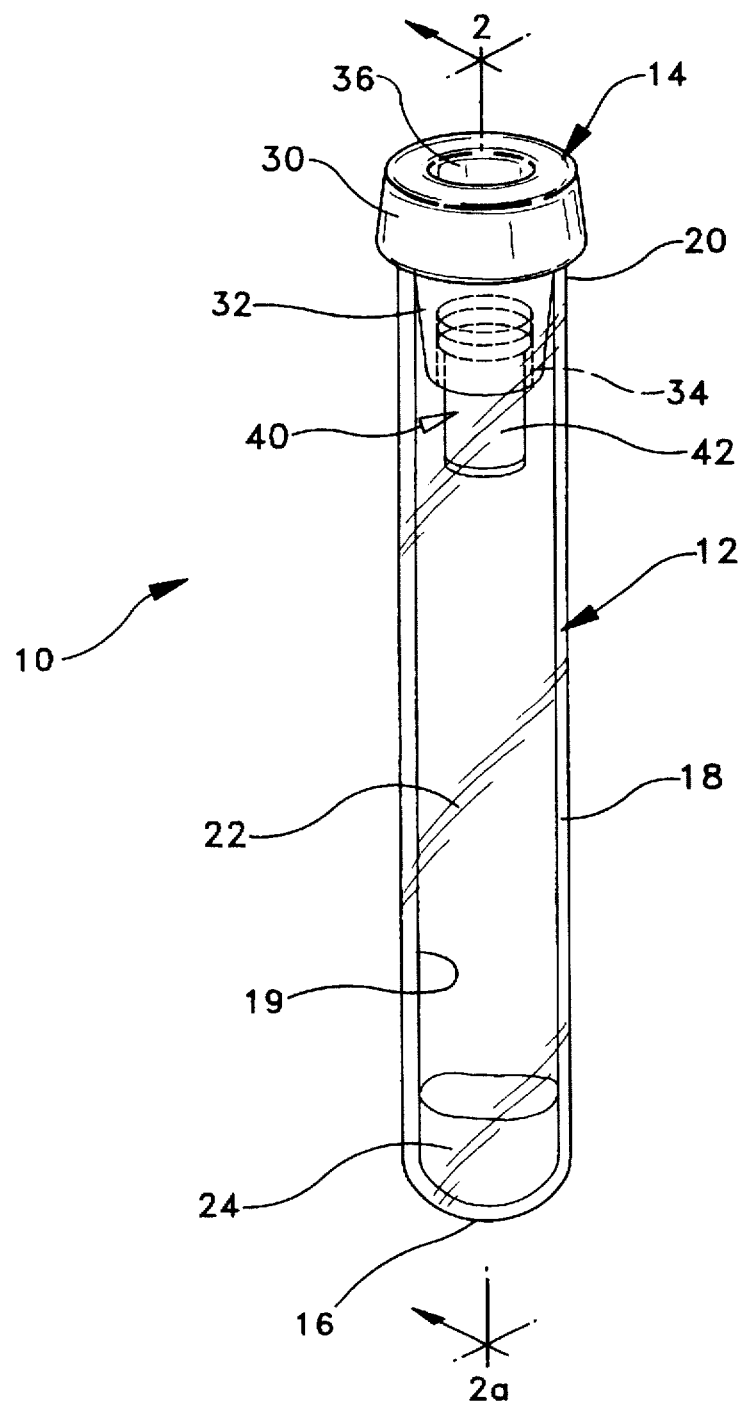
FIG. 1 is a perspective view of a blood collection assembly with a receptacle of the invention therein.
Figure 2:
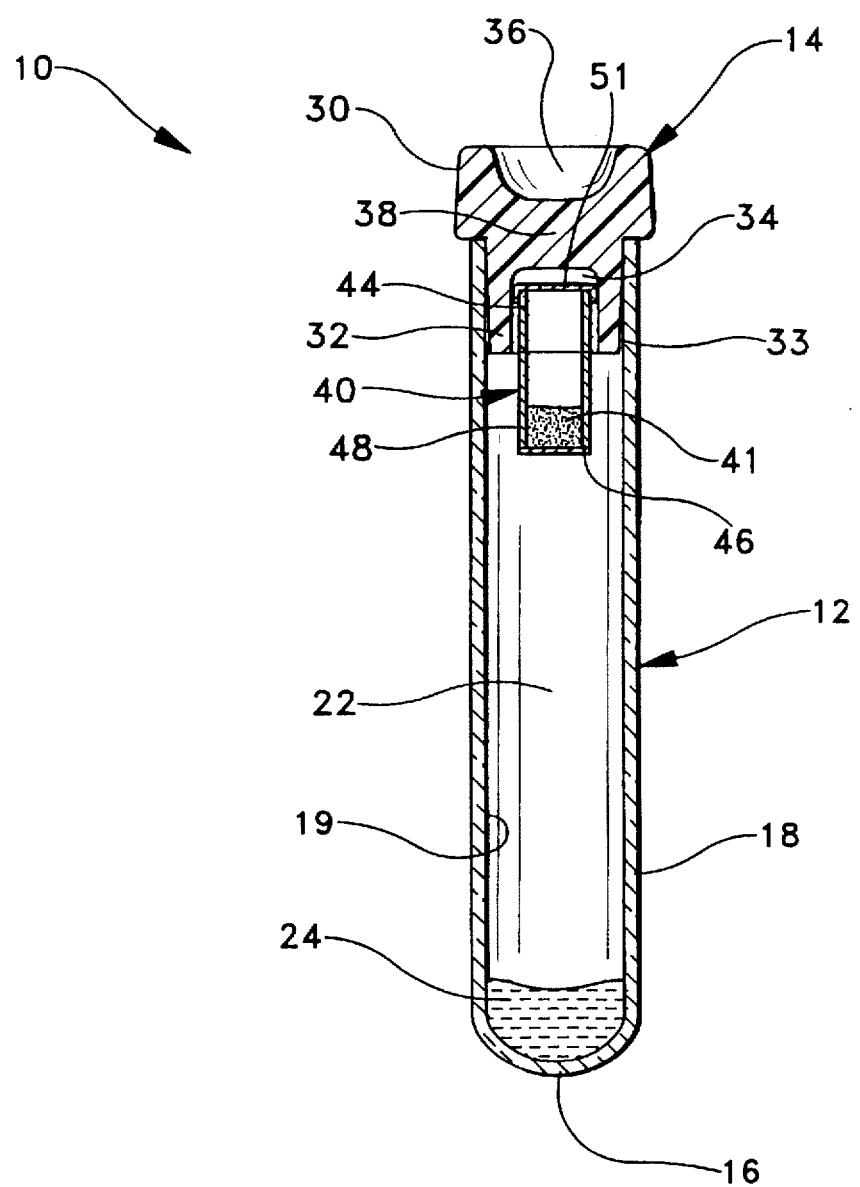
FIG. 2 is a vertical sectional view of the assembly of FIG. 1 taken along the line 2–2a thereof.

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having a closed end and an open end. Suitable containers are, for example bottles, vials, flasks and the like, preferably tubes. The container contains structure for storing an additive useful in preservation, separation or analysis of a blood sample taken in the container. The invention will henceforth be described in terms of the preferred tube.

Adverting now the drawings, FIG. 1 to 5 illustrate a blood collection assembly 10 which includes a tube 12 and a puncturable stopper 14. Tube 12 has a bottom wall 16 and a side wall 18 having an inside wall surface 19. Side wall 18 defines an open end 20 into which the stopper 14 may be placed. Bottom wall 16, side wall 18 and stopper 14 enclose an interior volume 22 of the tube which preferably contains a conventional serum separating gel 24 and preferably is evacuated. Evacuated tubes for blood collection are standard in the art.

Stopper 14 includes an annular upper portion 30 which extends over the top edge of side wall 18 and a lower annular portion or skirt 32 which extends into and forms an interference fit with inside wall surface 19 for maintaining stopper 14 in place in open end 20. Annular skirt 32 has a side wall 33 which defines a well 34. Annular upper portion 30 defines a cavity 36. A septum portion 38 of annular upper portion 30 extends between well 34 and cavity 36 for puncture by a cannula (as described later).

A receptacle 40 for storage and delivery of an additive 41 for blood analysis may be immobilized in well 34. As shown in FIGS. 3 and 4, receptacle 40 may be a tube or barrel portion 42 having open top end 44, a frangible bottom end 46 integral with a side wall 48. A preferred receptacle also has an optional covering 51 over top end 44, shown in FIGS. 3 and 4 as a closure which fits snugly in open end 44. Liquid additive 41 may be maintained in the receptacle.

In an alternate preferred embodiment of the invention, the receptacle may be in the form of a frangible ampoule. As shown in FIG. 5, the ampoule has integral bottom end 46a, side wall 48a and a top wall 51a and encloses additive 41a. (In FIGS. 5–10, elements similar to those previously described are given the same reference number followed by a letter suffix).

Receptacle 40 may be removably immobilized in well 34 by an interference fit between receptacle side wall 48 and side wall 33 of skirt 32. If receptacle 40 does not include optional covering 51, immobilization also includes a seal formed between the top of receptacle side wall 48 and septum portion 38 of annular upper portion 30 of stopper 14.

Figure 6:
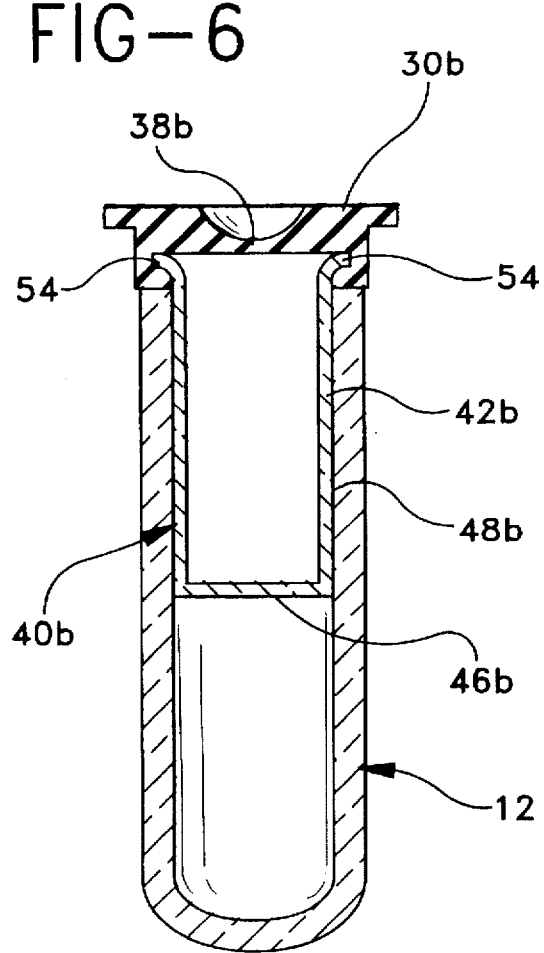
FIGS. 6 and 7 are vertical sectional views of alternate embodiments of the assembly of FIG. 1 taken along the lines 6–6a and 7–7a thereof.
Figure 7:
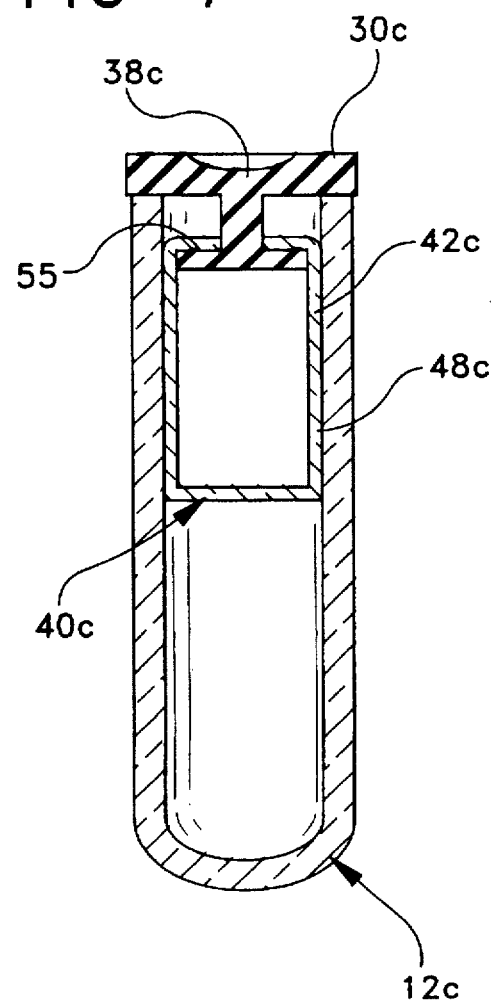
Figure 8:
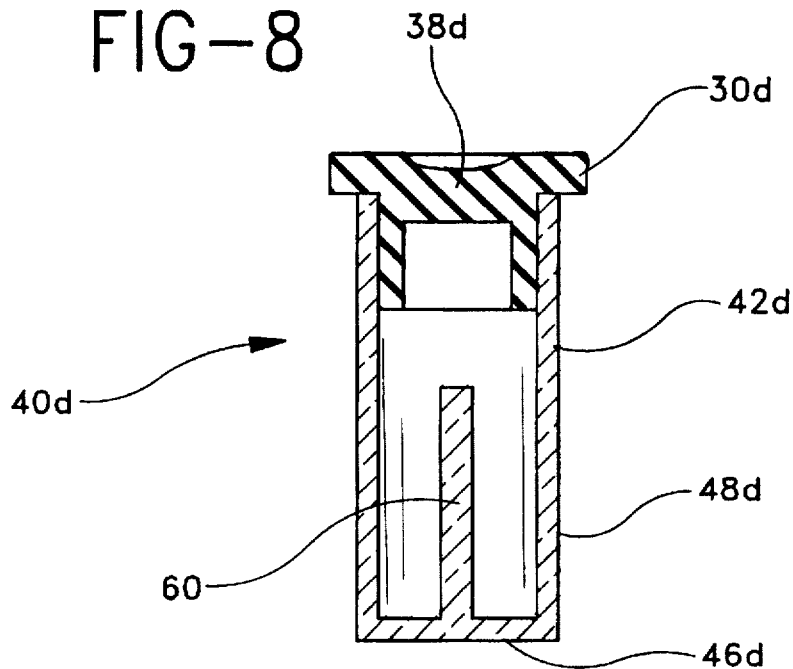
FIG. 8 is a sectional view of an alternate embodiment of the receptacle.

Without wishing to be limited thereby, a variety of alternative stopper-reservoir designs for removable immobilization of the receptacle are contemplated by the invention. For example, FIGS. 6 and 7 illustrate the receptacle to have outwardly and inwardly pointing lips 54 and 55 which mate with modified stoppers 30b and 30c respectively. FIG. 8 illustrates a modification of the receptacle in which a tab 60 projects upwardly from bottom wall 46d of reservoir 40d to engage the cannula during use, as described below. The tab may of course also project inwardly from the side wall. FIGS. 6–8 illustrate embodiments of the receptacle which do not include the top wall.

Figure 9:
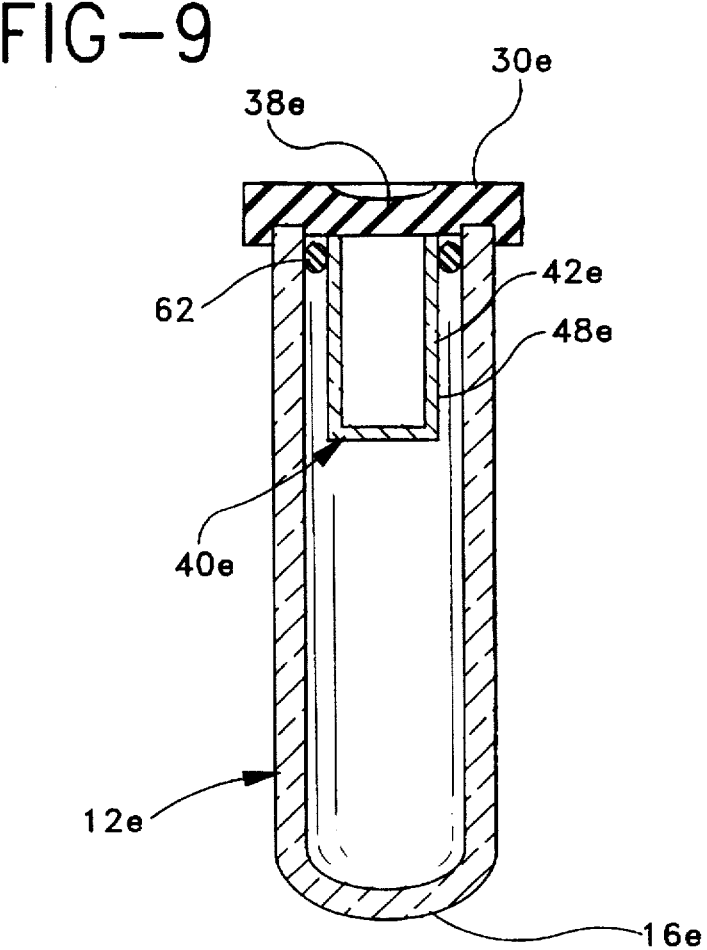
FIG. 9 illustrates an alternate embodiment of the assembly.

In FIG. 9, receptacle 40e is removably immobilized in tube 12e by an elastomeric O-ring, 62.

The tube may be of glass or preferably plastic. Suitable plastics are polypropylene (PP), polyethylene terephthalate (PET) and polystyrene (PS). While the tube may be of any size, the invention is particularly well suited to evacuated blood collection tubes. These tubes are generally cylindrical, 50 to 150 mm in length and about 10 to 20 mm in diameter. The stopper may be of any elastomer, as is well known in the art of evacuated blood collection tubes.

The receptacle may be of a moisture and gas impermeable material such as plastic, metal, ceramic or glass. The receptacle may be of any size suitable for holding the additive to be dispensed. Preferred receptacles for the above-described standard blood collection tubes have a capacity of about 600 uL and may be of glass tubing (0.6 cm OD, 0.5 cm ID and about 0.5 to 2.0 cm in length). These dimensions allow the receptacle to fit into the well within the skirt portion of conventional blood collection tube stoppers with an axial orientation for accessibility to the blood draw cannula.

Any additive useful in blood analysis, including both procoagulants and anticoagulants, may be stored in the receptacle. In this way, the assembly, by proper selection of additive, may be used across the entire spectrum of commercial blood collection tubes. While the additives may be supplied in the receptacle in any desired form, such as a powdered, crystalline or lyophilized solid, the invention is particularly suitable for dispensing additives in solution, such as a solution in water or saline.

As known in the art, blood analysis is often performed on serum, and procoagulants are often used to enhance the rate of clotting. A representative but not exhaustive list of suitable procoagulants which may be stored in the receptacle are particulate clot activators such as silica particles or enzyme clot activators such as elegiac acid, fibrinogen and thrombin.

On the other hand, if plasma is needed for analysis, an anticoagulant is generally provided to inhibit coagulation while blood cells are removed by centrifugation. Suitable anticoagulants for the present invention may be, for example, chelators such as oxalates, citrate, and EDTA or enzymes such as heparin.

The choice and quantity of additive to be stored in the receptacle depends on the size of the blood sample and analytical procedure to be performed and are well known to those skilled in the blood analysis art. No further details are needed for a full understanding of this aspect of the invention.

Figure 10:
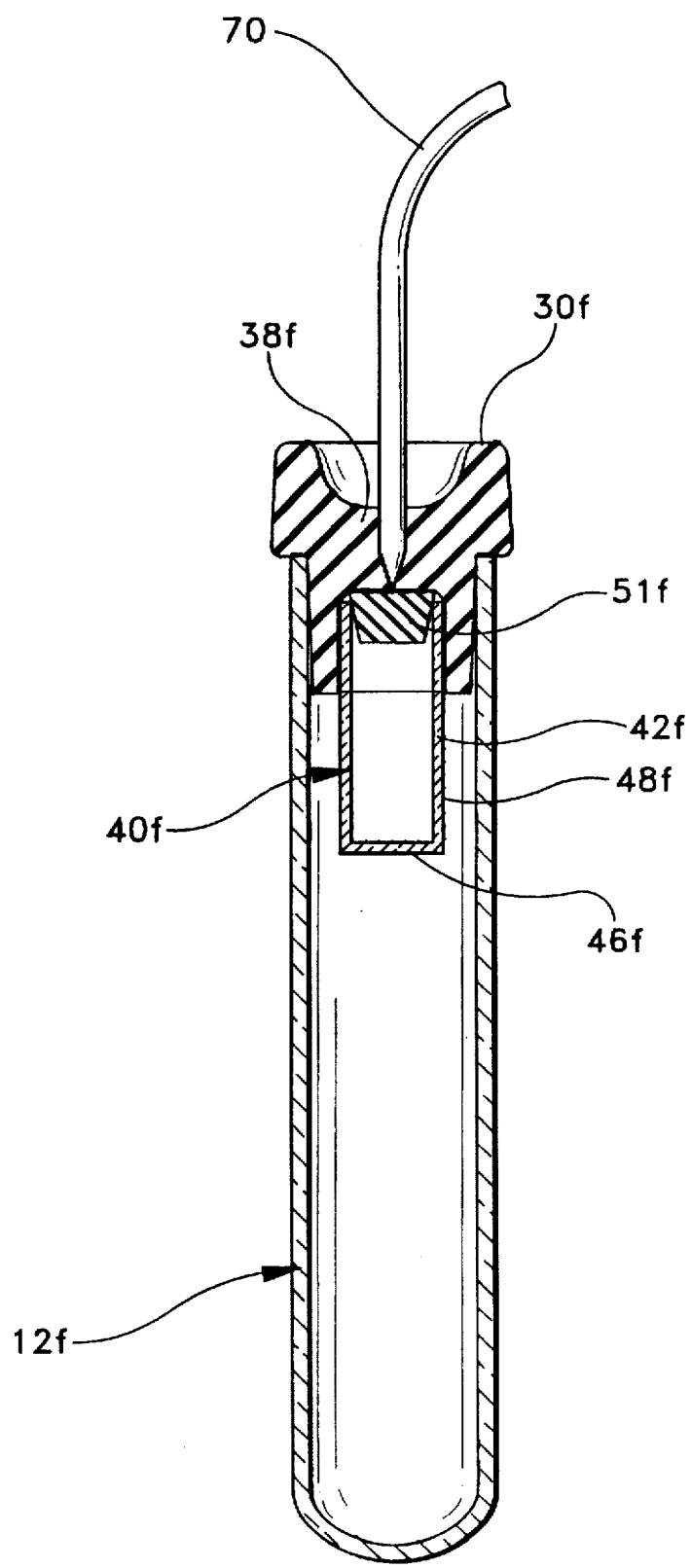
FIG. 10 is a vertical sectional view of the assembly of FIG. 1 showing puncture of the stopper and receptacle by a cannula.
Figure 11:
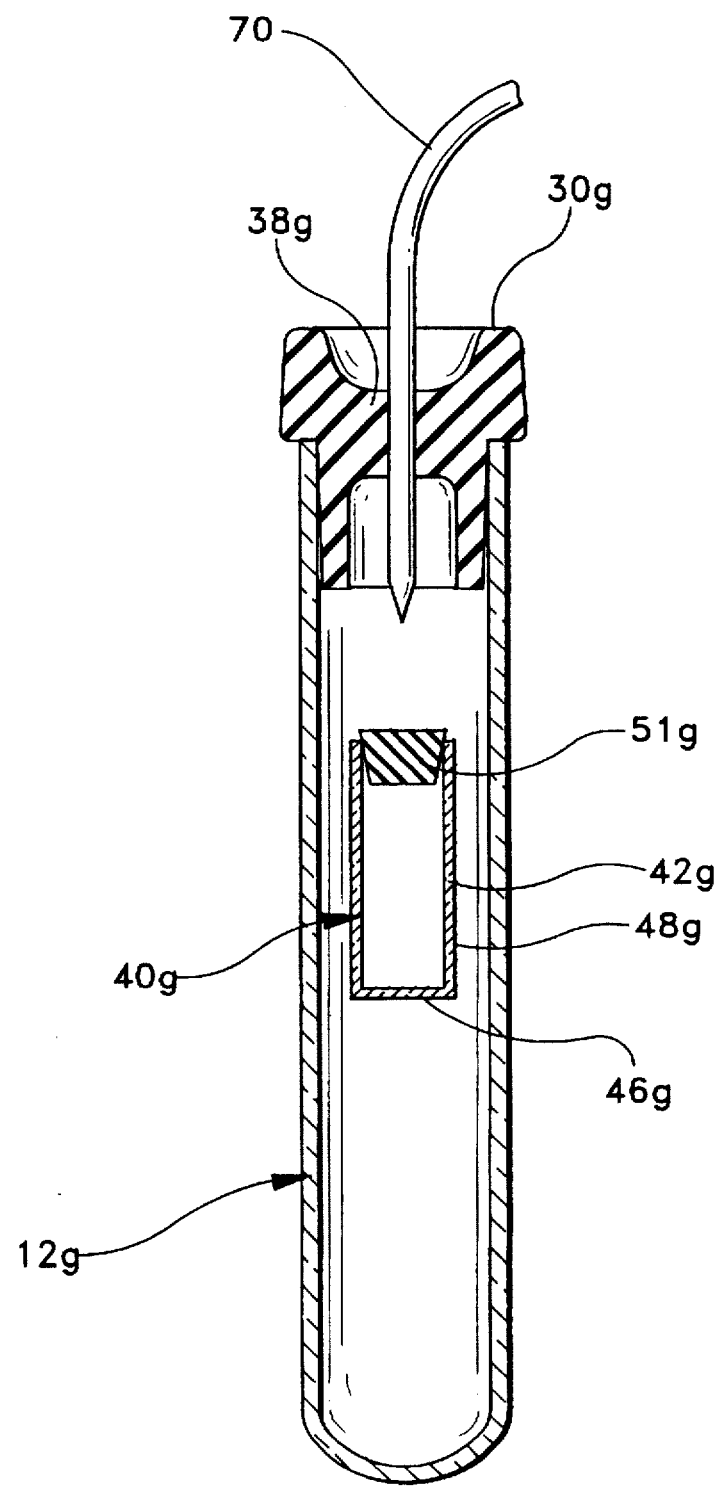
FIG. 11 is a vertical sectional view of the assembly of FIG. 1 after the receptacle has been dislodged from the stopper.

As mentioned above, the septum portion of the stopper is pierced by a cannula during blood sampling. In use of the assembly, the receptacle is dislodged from the stopper and falls to the bottom of the tube, shatters and releases the additive. The receptacle may be dislodged by manual application of pressure to septum 38. Preferably, release of the receptacle is accomplished at the same time that septum 38 is pierced by the cannula. As illustrated in FIG. 10, one end of a cannula 70 is connected to a blood supply such as of a patient's vein (not shown in the drawing), and the other end is inserted by puncture through septum 38f. If the assembly includes the optional covering over the open end of the receptacle, shown in FIG. 10 as closure 51f, the cannula will, after puncture of septum 38f abut this covering. Forward pressure applied to cannula, 70 overcomes the interference fit between stopper 30f and receptacle side wall 48f. As shown in FIG. 11, receptacle 40f is thereby dislodged from the stopper and falls to the bottom of tube 12f, shattering frangible bottom wall 46f. Alternatively, the tube vacuum can cause removal of closure 51f to release the contents of the receptacle. Blood immediately flows from the cannula into the tube and mixes with liquid additive 41f released from the broken receptacle. For the embodiment of the invention in which the receptacle is in the form of an ampoule (FIG. 5), pressure exerted on the integral top wall dislodges the receptacle and causes it to fall and shatter.

If the receptacle has an open top end so that the stopper septum provides the top wall, as shown in FIG. 8, it is preferred that the receptacle include tab 60 for engagement with the cannula to dislodge the receptacle. However, as mentioned above, the tab may be configured with other geometries than upwardly projecting tab 60. If the receptacle does not include covering 51 or tab 60, the cannula, after piercing septum 38, abuts the bottom wall of the receptacle, which is dislodged by forward pressure.

Other arrangements for release of the receptacle contemplated by the invention include positioning a magnetic bead in the receptacle (not shown in the drawings) so that a magnetic field can be used to dislodge the receptacle. In still another embodiment, the assembly may be microwaved prior to cannula piercing so that the liquid additive heats up and increased vapor pressure causes the receptacle to burst. Alternatively, the receptacle my be removably immobilized with an adhesive (not shown in the drawings), which softens on microwave treatment to release the receptacle.

In the preferred assembly of the invention, the tube is plastic, preferably PET, and the receptacle is glass. Thus, the preferred tube has the advantages of plastic, but the disadvantage of plastic, water permeability, is overcome because any water soluble additive is stored in the water impermeable glass receptacle, and no deterioration or dilution of the additive takes place.

What is claimed is:

1. A blood collection assembly comprising:
   a) and evacuated container having a bottom wall and a side wall defining an open end;
   b) a puncturable stopper in said open end, said bottom wall, side wall and stopper enclosing an interior volume in said container; and
   c) a liquid impermeable receptacle removably immobilized in said stopper, said receptacle comprising a glass side wall defining an open end, a top wall covering said open end, and a frangible glass bottom wall constructed as one piece with said side wall.

2. The assembly of claim 1 further comprising an additive in said receptacle for use in analysis of blood.

3. The assembly of claim 1 wherein said top wall is a closure in said open end.

4. The assembly of claim 1 wherein said top wall is of glass and is constructed as one piece with said side and bottom walls.

5. A blood collection assembly comprising:
   a) an evacuated tube having a bottom wall and a side wall defining an open end;
   b) a puncturable stopper in said open end, said bottom wall, side wall and stopper enclosing an interior volume in said tube, said stopper comprising an annular puncturable upper portion and a lower skirt portion, said skirt portion defining a well;
   c) a liquid impermeable glass ampoule removably immobilized in said well, said ampoule having top, side and bottom walls constructed as one piece; and
   d) an additive in said ampoule for use in analysis of blood.

6. The assembly of claim 5 wherein said ampoule is removably immobilized in said well by an interference fit.

* * * * *